United States Patent [19]

Mihailovski

[11] B 3,991,195
[45] Nov. 9, 1976

[54] METHOD OF CONTROLLING BACTERIA

[75] Inventor: Alexander Mihailovski, Berkeley, Calif.

[73] Assignee: Stauffer Chemical Company, Westport, Conn.

[22] Filed: May 6, 1974

[21] Appl. No.: 466,929

[44] Published under the second Trial Voluntary Protest Program on January 27, 1976 as document No. B 466,929.

[52] U.S. Cl. .............................. 424/263; 260/295 E
[51] Int. Cl.² ............................................. A01N 9/22
[58] Field of Search ................................... 424/263

[56] References Cited
UNITED STATES PATENTS
3,700,678 10/1972 Mihailovski .................... 260/295 E Primary Examiner—Leonard Schenkman
Attorney, Agent, or Firm—Daniel C. Block

[57] ABSTRACT

This invention relates to the method of controlling bacteria comprising adding to the habitat thereof an effective amount of a compound having the formula:

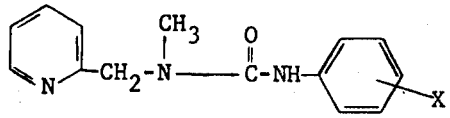

wherein X is selected from 4-trifluoromethyl, 3-nitro and 3-trifluoromethyl.

4 Claims, No Drawings

METHOD OF CONTROLLING BACTERIA

DESCRIPTION OF THE INVENTION

The process of synthesizing the compounds of this invention is described in prior U.S. Pat. No. 3,700,678. The compounds are described as having herbicidal activity.

This invention relates to a new use of these compounds. More specifically, it has been discovered that these compounds are highly effective bacteriostats. The compounds embraced by this invention have the following formulas:

Compound No. 1

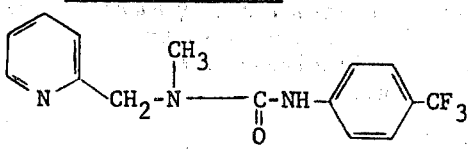

Compound No. 2

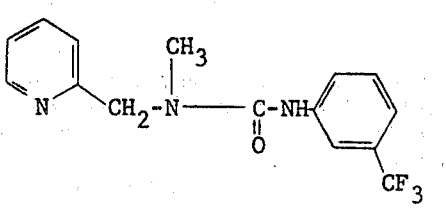

Compound No. 3

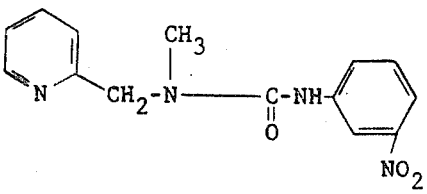

BIOCIDE TESTING PROCEDURES

Tubes of sterilized nutrient broth are prepared. Aliquots of the toxicant, dissolved in an appropriate solvent, are injected through the stopper, into the broth, to provide concentrations ranging from 50 ppm downward. The test organism consisted of *Staphylococcus aureus* (S.a.) Rosenbach. Three drops of bacteria are injected into the nutrient broth. One week later the growth of each organism is observed and effectiveness of the chemical is recorded as the lowest concentration in ppm which provides 50% inhibition of growth as compared to untreated inoculated tubes. The results of these tests are tabulated in Table I.

TABLE I

| | |
|---|---|
| Compound No. 1 | 0.25 |
| Compound No. 2 | 5.00 |
| Compound No. 3 | 25.00 |

In Vitro Agar Screening Tests

This test measures the bactericidal properties of a compound when in contact with growing bacteria in an artificial medium. The test is conducted by adding 20 ml. portions of a suitable warm sterile agar solution into 20 × 100 mm. Petri dishes. Then, the test compound, in 0.5% acetone solution, is added to the Petri dishes at levels of 1, 5, 10 and 50 µg/ml. and mixed with the warm mobile agar solution. The treated agar mixture is then allowed to come to room temperature and solidify. Cells of the chosen organism are streaked on the surface of the solidified agar and are then incubated for such lengths of time that untreated samples containing no toxicant shows luxurious growth typical of the particular organism. This time varies from 24 hours to one week depending on the particular organism. The bacteria are incubated at 37° C in nutrient agar as the medium in this test.

The extent of growth is noted at the end of the incubation period.

Representative organisms used in this test are as follows:

Bacteria
  *Enterobacter aerogenes*
  *Bacillus cereus*
  *Pseudomonas aeruginosa*
  *Brevibacterium ammoniagenes*
  *Staphylococcus aureus*
  *Escherichia coli*

TABLE II

In Vitro Agar Screening Tests

| Bacteria | Minimum Inhibitory Concentration, µg/ml. Compound I |
|---|---|
| *Enterobacter aerogenes* | (50) |
| *Bacillus cereus* | 5 |
| *Pseudomonas aeruginosa* | >50 |
| *Brevibacterium ammoniagenes* | 10 |
| *Staphylococcus aureus* | 5 |
| *Escherichia coli* | >50 |

( )indicates partial control at this concentration
>greater than

Sulfate Reducing Bacteria In Vitro Test

This test measures the bactericidal properties of a compound when in contact with a sulfate reducing bacteria, specifically *Desulfovibrio desulfuricans*. The test is conducted by dissolving the test compound in acetone to give an 0.5% solution. This toxicant is added to vials containing sterile Sulfate API broth with tryptone under anaerobic conditions at such levels to give final toxicant concentrations of 1, 5, 10 and 50 µg/ml. of solution. An inoculant solution of 0.5 ml. of the growing organism, *Desulfovibrio desulfuricans*, is added to the vials followed by sufficient sterile distilled water to give a total of 10 ml. of solution in the vials. The vials are incubated at room temperature for 3 to 5 days until untreated controls show growth of the organism as indicated by the black color development in the vials.

The following is a summary of the minimum inhibitory concentration necessary to control the organism.

TABLE III

|  | Example I |
|---|---|
| *Desulfovibrio desulfuricans* | 50 |

The compounds of this invention are generally embodied into a form suitable for convenient application. For example, the compounds can be embodied into pesticidal compositions which are provided in the form of emulsions, suspensions, solutions, dusts and aerosol sprays. In general, such compositions will contain, in addition to the active compound, the adjuvants which are found normally in pesticide preparations. In these compositions, the active compounds of this invention can be employed as the sole pesticide component or they can be used in admixture with other compounds having similar utility. The pesticide compositions of this invention can contain, as adjuvants, organic solvents such as sesame oil, xylene range solvents, heavy petroleum, etc; water; emulsifying agents; surface active agents; talc; pyrophyllite; diatomite; gypsum; clays; propellants, such as dichlorodifluoromethane, etc. If desired, however, the active compounds can be applied directly to feedstuffs, seeds, etc. upon which the pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active pesticide in the present compositions can vary within rather wide limits, ordinarily the pesticide compound will comprise not more than about 15.0% by weight of the composition. Preferably, however, the pesticide compositions of this invention will be in the form of solutions or suspensions containing about 0.1 to 1.0% by weight of the active pesticide compound.

What is claimed is:

1. A method of inhibiting the growth of bacteria selected from the group consisting of *Bacillus cereus*, *Brevibacterium ammoniagenes*, *Staphylococcus aureus* and *Desulfovibrio desulfuricans* comprising contacting the bacteria with an effective amount of a compound having the formula:

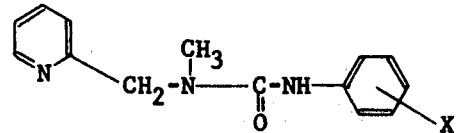

wherein X is selected from the group consisting of 4-trifluoromethyl, 3-nitro and 3-trifluoromethyl.

2. The method of claim 1 wherein X is 4-trifluoromethyl.

3. The method of claim 1 wherein X is 3-nitro.

4. The method of claim 1 wherein X is 3-trifluoromethyl.

* * * * *